(12) United States Patent
Hirashima et al.

(10) Patent No.: US 7,960,508 B2
(45) Date of Patent: Jun. 14, 2011

(54) PEPTIDE HAVING CYTOTOXICITY INHIBITORY ACTIVITY AND METHOD OF SCREENING THESE PEPTIDE HAVING CYTOTOXICITY INHIBITORY ACTIVITY

(75) Inventors: Masaki Hirashima, Kumamoto-ken (JP); Takeshi Naruse, Kumamoto-ken (JP); Hiroaki Maeda, Kumamoto-ken (JP); Chikateru Nozaki, Kumamoto-ken (JP); Takeshi Goto, Tsukuba (JP); Katsuhiko Akiyama, Tsukuba (JP); Wataru Hattori, Tsukuba (JP)

(73) Assignees: Juridical Foundation The Chemo-Sero-Therapeutic Research Institute, Kumamoto-Shi (JP); Hisamitsu Pharmaceutical Co., Inc., Tosu-Shi (JP)

( * ) Notice: Subject to any disclaimer, the term of this patent is extended or adjusted under 35 U.S.C. 154(b) by 0 days.

(21) Appl. No.: 10/477,101

(22) PCT Filed: May 10, 2002

(86) PCT No.: PCT/JP02/04557
§ 371 (c)(1),
(2), (4) Date: Nov. 10, 2003

(87) PCT Pub. No.: WO02/092810
PCT Pub. Date: Nov. 21, 2002

(65) Prior Publication Data
US 2005/0143311 A1   Jun. 30, 2005

(30) Foreign Application Priority Data

May 11, 2001 (JP) ................................. 2001-141466

(51) Int. Cl.
*A61K 38/00* (2006.01)
*A61K 38/04* (2006.01)
*A61K 38/16* (2006.01)
*A61K 38/10* (2006.01)
*C07K 5/00* (2006.01)
*C07K 7/00* (2006.01)
*C07K 16/00* (2006.01)
*C07K 17/00* (2006.01)

(52) U.S. Cl. ..................... 530/329; 514/21.3; 514/21.4
(58) Field of Classification Search .................. None
See application file for complete search history.

(56) References Cited

U.S. PATENT DOCUMENTS

| 5,405,772 | A | * | 4/1995 | Ponting ........................... 435/378 |
| 5,861,268 | A | * | 1/1999 | Tang et al. ....................... 435/25 |
| 7,199,097 | B1 | * | 4/2007 | Hirashima et al. ............... 514/2 |
| 2005/0037954 | A1 | * | 2/2005 | Hirashima et al. ............. 514/12 |
| 2005/0143310 | A1 | * | 6/2005 | Hirashima et al. ............. 514/14 |
| 2005/0143311 | A1 | * | 6/2005 | Hirashima et al. ............. 514/15 |

FOREIGN PATENT DOCUMENTS

| EP | 1 132 402 A1 | | 9/2001 |
| WO | WO 00/31131 | * | 2/2000 |
| WO | WO00/31131 | * | 6/2000 |
| WO | WO 00/31131 A1 | | 6/2000 |

OTHER PUBLICATIONS

Andreadou et al. Comparative Cytotoxicity of 14 Novel Selenocysteine Se-Conjugates in Rat Renal Proximal Tubular Cells. Toxicology and Applied Pharmacology. 1996. vol. 141, pp. 278-287.*
Siddiqui et al. Docosahexaenoic acid induces apoptosis in Jurkat cells by a protein phosphatase-mediated process. Biochim Biophys Acta 2001. vol. 1499, No. 3. pp. 265-275.*
Kim et al. Inhibition of c-Jun Expression Induces Antioxidant Enzymes under Serum Deprivation. Archives of Biochemsitry and Biophysics. Feb. 2000. vol. 374. No. 2, pp. 339-346.*
Park et al. Thymic peptide modulates glutathione redox cycle and antioxidant enzymes in macrophages. J Leukocyte Biology. Apr. 1994. vol. 55, pp. 496-500.*
Descampiaux et al. Cytotoxicity of Lindane and Paraquat to Human Hepatoma Cell Lines. Bull. Environ. Contam. Toxicol. 1999. vol. 62, pp. 16-24.*
Wirth. Gluthathione Peroxidase-like Activities of Oxygen-Containing Diselenides. Molecules, 1998. vol. 3, pp. 164-166.*
Lee. Gluthathione S-transferase and glutathione peroxidase are essential in the early stage of Adriamycin resistance before P-glycoprotein overexpression in HOB1 lymphoma cells. Cancer Chemother Pharmacol. 1996, vol. 38, pp. 45-51.*
Asahi et al. The Oxidation of Selenocysteine Is Involved in the Inactivation of Glutathione Peroxidase by Nitric Oxide Donor. The Journal of Biological Chemistry. 1997. vol. 272. pp. 19152-19157.*
Stewart et al. Selenium compounds have disparate abilities to impose oxidative stress and induce apoptosis. Free Radical Biology and Medicine. 1999. vol. 26, pp. 42-48.* West et al. Adrenergic, Cholinergic, and Inactive Human Neuroblastoma Cell Lines with the Action-Potential Na+ Ionophore. Cancer Research, May 1977, vol. 37, pp. 1372-1376.*
Ellsworth et al. Very low and low density lipoprotein synthesis and secretion by the human hepatoma cell line Hep-G2: effects of free fatty acid. Journal of Lipid Research, 1986, vol. 27, pp. 858-874.*
Jun Yan et al.; The Journal of Neuroscience, vol. 18, No. 21, Nov. 1, 1998, pp. 8682-8691.
Masaki Hirashima et al.; Biological & Pharmaceutical Bulletin, vol. 26, No. 6, Jun. 2003, pp. 794-798.
Volker Mostert; Archives of Biochemistry and Biophysics, vol. 376, No. 2, Apr. 15, 2000, pp. 433-438.
Yangxin Fu et al.; Free Radical Biology and Medicine, vol. 27, No. 5-6, Sep. 1999, pp. 605-611.

(Continued)

*Primary Examiner* — Marcela M Cordero Garcia
(74) *Attorney, Agent, or Firm* — Birch, Stewart, Kolasch & Birch, LLP (57) ABSTRACT

A peptide fragment or a series of peptide fragments containing one or more selenocysteine that has a lowered toxicity than selenocystine and that exhibits a cytotoxicity-inhibitory activity. The peptide fragment or a series of peptide fragments according to the present invention has preferably the amino acid sequence from 260th to 362nd amino acid residues from the C-terminal of selenoprotein P, or said amino acid sequence with one or several amino acid residues therein being deleted, substituted or added, or a partial sequence of either of the above amino acid sequences, or an amino acid sequence comprising as a part any of the above amino acid sequences. A screening method for a peptide fragment having the cytotoxicity-inhibitory activity is also provided.

20 Claims, 4 Drawing Sheets

OTHER PUBLICATIONS

Rudra P K et al., "Cell-Specific Enhancement of Doxorubicin Toxicity in Human Tumor Cells by Docosahexaenoic Acid." Anticancer Research, Jan.-Feb. 2001, 21(1A):29-38, XP009077371.

Maulik Nilanjana et al., "Regulation of Cardiomyocyte Apoptosis in Ischemic Reperfused Mouse Heart by Glutathione Peroxidase." Molecular and Cellular Biochemistry, 196(1-2): 13-21, Jun. 1999, XP002415317.

Kayanoki Y et al., "The protective Role of Glutathione Peroxidase in Apoptosis Induced by Reactive Oxygen Species," Journal of Biochemistry, Apr. 1996, 119(4):817-822, XP009077379.

Siddiqui et al., Docosahexaenoic acid induces apoptosis in Jurkat cells by a protein phosphatase-mediated process, Biochemica et Biophysica Acta, Jan. 2001, vol. 1499, No. 3, pp. 265-275.

Morimoto et al., Fuhowa Shibosan Kasankabutsu oyobi Lin-shishitsu Kasankabutsu ni yoru Baiyo Hakkekyu Saibo U937 no Saiboshi Yudo, Journal of lipid nutrition, 2000, vol. 9, No. 2, p. 119.

Kim et al., Inhibition of c-Jun expression induces antioxidant enzymes under serum deprivation, Archives of Biochemistry and Biophysics, 2000, vol. 374, No. 2, pp. 339-346.

* cited by examiner

SEQUENCE LISTING

```
<160> NUMBER OF SEQ ID NOS: 17

<210> SEQ ID NO 1
<211> LENGTH: 14
<212> TYPE: PRT
<213> ORGANISM: Human plasma
<220> FEATURE:
<221> NAME/KEY: misc_feature
<222> LOCATION: (3)..(3)
<223> OTHER INFORMATION: Xaa represents selenocysteine

<400> SEQUENCE: 1

Arg Ser Xaa Cys Cys His Cys Arg His Leu Ile Phe Glu Lys
1               5                   10

<210> SEQ ID NO 2
<211> LENGTH: 103
<212> TYPE: PRT
<213> ORGANISM: Human plasma
<220> FEATURE:
<221> NAME/KEY: misc_feature
<222> LOCATION: (1)..(103)
<223> OTHER INFORMATION: Fragment of selenoprotein P - residues 260
      through 362
<220> FEATURE:
<221> NAME/KEY: misc_feature
<222> LOCATION: (22)..(22)
<223> OTHER INFORMATION: Xaa represents selenocysteine
<220> FEATURE:
<221> NAME/KEY: misc_feature
<222> LOCATION: (40)..(40)
<223> OTHER INFORMATION: Xaa represents selenocysteine
<220> FEATURE:
<221> NAME/KEY: misc_feature
<222> LOCATION: (52)..(52)
```

-continued

```
<223> OTHER INFORMATION: Xaa represents selenocysteine
<220> FEATURE:
<221> NAME/KEY: misc_feature
<222> LOCATION: (67)..(67)
<223> OTHER INFORMATION: Xaa represents selenocysteine
<220> FEATURE:
<221> NAME/KEY: misc_feature
<222> LOCATION: (74)..(74)
<223> OTHER INFORMATION: Xaa represents selenocysteine
<220> FEATURE:
<221> NAME/KEY: misc_feature
<222> LOCATION: (89)..(89)
<223> OTHER INFORMATION: Xaa represents selenocysteine
<220> FEATURE:
<221> NAME/KEY: misc_feature
<222> LOCATION: (91)..(91)
<223> OTHER INFORMATION: Xaa represents selenocysteine
<220> FEATURE:
<221> NAME/KEY: misc_feature
<222> LOCATION: (98)..(98)
<223> OTHER INFORMATION: Xaa represents selenocysteine
<220> FEATURE:
<221> NAME/KEY: misc_feature
<222> LOCATION: (100)..(100)
<223> OTHER INFORMATION: Xaa represents selenocysteine

<400> SEQUENCE: 2

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
                20                  25                  30

Lys Thr Gly Ser Ala Ile Thr Xaa Gln Cys Lys Glu Asn Leu Pro Ser
            35                  40                  45

Leu Cys Ser Xaa Gln Gly Leu Arg Ala Glu Glu Asn Ile Thr Glu Ser
        50                  55                  60

Cys Gln Xaa Arg Leu Pro Pro Ala Ala Xaa Gln Ile Ser Gln Gln Leu
65                  70                  75                  80

Ile Pro Thr Glu Ala Ser Ala Ser Xaa Arg Xaa Lys Asn Gln Ala Lys
                85                  90                  95

Lys Xaa Glu Xaa Pro Ser Asn
            100

<210> SEQ ID NO 3
<211> LENGTH: 33
<212> TYPE: PRT
<213> ORGANISM: Human plasma
<220> FEATURE:
<221> NAME/KEY: misc_feature
<222> LOCATION: (22)..(22)
<223> OTHER INFORMATION: Xaa represents selenocysteine

<400> SEQUENCE: 3

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
                20                  25                  30

Lys

<210> SEQ ID NO 4
<211> LENGTH: 21
<212> TYPE: PRT
<213> ORGANISM: Human plasma

<400> SEQUENCE: 4

Lys Arg Cys Ile Asn Gln Leu Leu Cys Lys Leu Pro Thr Asp Ser Glu
1               5                   10                  15
```

Leu Ala Pro Arg Ser
            20

<210> SEQ ID NO 5
<211> LENGTH: 14
<212> TYPE: PRT
<213> ORGANISM: Human plasma

<400> SEQUENCE: 5

Arg Ser Ser Cys Cys His Cys Arg His Leu Ile Phe Glu Lys
1               5                   10

<210> SEQ ID NO 6
<211> LENGTH: 14
<212> TYPE: PRT
<213> ORGANISM: Human plasma
<220> FEATURE:
<221> NAME/KEY: misc_feature
<222> LOCATION: (3)..(3)
<223> OTHER INFORMATION: Xaa represents selenocysteine

<400> SEQUENCE: 6

Arg Ser Xaa Ser Cys His Cys Arg His Leu Ile Phe Glu Lys
1               5                   10

<210> SEQ ID NO 7
<211> LENGTH: 14
<212> TYPE: PRT
<213> ORGANISM: Human plasma
<220> FEATURE:
<221> NAME/KEY: misc_feature
<222> LOCATION: (3)..(3)
<223> OTHER INFORMATION: Xaa represents selenocysteine

<400> SEQUENCE: 7

Arg Ser Xaa Ser Ser His Cys Arg His Leu Ile Phe Glu Lys
1               5                   10

<210> SEQ ID NO 8
<211> LENGTH: 14
<212> TYPE: PRT
<213> ORGANISM: Human plasma
<220> FEATURE:
<221> NAME/KEY: misc_feature
<222> LOCATION: (3)..(3)
<223> OTHER INFORMATION: Xaa represents selenocysteine

<400> SEQUENCE: 8

Arg Ser Xaa Ser Ser His Ser Arg His Leu Ile Phe Glu Lys
1               5                   10

<210> SEQ ID NO 9
<211> LENGTH: 4
<212> TYPE: PRT
<213> ORGANISM: Human plasma
<220> FEATURE:
<221> NAME/KEY: misc_feature
<222> LOCATION: (3)..(3)
<223> OTHER INFORMATION: Xaa represents selenocysteine

<400> SEQUENCE: 9

Arg Ser Xaa Ser
1

<210> SEQ ID NO 10
<211> LENGTH: 10
<212> TYPE: PRT
<213> ORGANISM: Human plasma
<220> FEATURE:

```
<221> NAME/KEY: misc_feature
<222> LOCATION: (7)..(7)
<223> OTHER INFORMATION: Xaa represents selenocysteine

<400> SEQUENCE: 10

Thr Gly Ser Ala Ile Thr Xaa Gln Ser Lys
1               5                   10

<210> SEQ ID NO 11
<211> LENGTH: 13
<212> TYPE: PRT
<213> ORGANISM: Human plasma
<220> FEATURE:
<221> NAME/KEY: misc_feature
<222> LOCATION: (9)..(9)
<223> OTHER INFORMATION: Xaa represents selenocysteine

<400> SEQUENCE: 11

Glu Asn Leu Pro Ser Leu Ser Ser Xaa Gln Gly Leu Arg
1               5                   10

<210> SEQ ID NO 12
<211> LENGTH: 12
<212> TYPE: PRT
<213> ORGANISM: Human plasma
<220> FEATURE:
<221> NAME/KEY: misc_feature
<222> LOCATION: (11)..(11)
<223> OTHER INFORMATION: Xaa represents selenocysteine

<400> SEQUENCE: 12

Ala Glu Glu Asn Ile Thr Glu Ser Ser Gln Xaa Arg
1               5                   10

<210> SEQ ID NO 13
<211> LENGTH: 11
<212> TYPE: PRT
<213> ORGANISM: Human plasma
<220> FEATURE:
<221> NAME/KEY: misc_feature
<222> LOCATION: (10)..(10)
<223> OTHER INFORMATION: Xaa represents selenocysteine

<400> SEQUENCE: 13

Leu Ile Pro Thr Glu Ala Ser Ala Ser Xaa Arg
1               5                   10

<210> SEQ ID NO 14
<211> LENGTH: 8
<212> TYPE: PRT
<213> ORGANISM: Human plasma
<220> FEATURE:
<221> NAME/KEY: misc_feature
<222> LOCATION: (7)..(7)
<223> OTHER INFORMATION: Xaa represents selenocysteine

<400> SEQUENCE: 14

Lys Asn Gln Ala Lys Lys Xaa Glu
1               5

<210> SEQ ID NO 15
<211> LENGTH: 4
<212> TYPE: PRT
<213> ORGANISM: Human plasma
<220> FEATURE:
<221> NAME/KEY: misc_feature
<222> LOCATION: (1)..(1)
<223> OTHER INFORMATION: Xaa represents selenocysteine

<400> SEQUENCE: 15
```

```
Xaa Pro Ser Asn
1

<210> SEQ ID NO 16
<211> LENGTH: 14
<212> TYPE: PRT
<213> ORGANISM: Human plasma
<220> FEATURE:
<221> NAME/KEY: misc_feature
<222> LOCATION: (12)..(12)
<223> OTHER INFORMATION: Xaa represents selenocysteine

<400> SEQUENCE: 16

Lys Glu Phe Ile Leu His Arg Ser His Ser Xaa Ser Arg
1               5                   10

<210> SEQ ID NO 17
<211> LENGTH: 11
<212> TYPE: PRT
<213> ORGANISM: Human plasma
<220> FEATURE:
<221> NAME/KEY: misc_feature
<222> LOCATION: (6)..(6)
<223> OTHER INFORMATION: Xaa represents selenocysteine

<400> SEQUENCE: 17

Leu Pro Pro Ala Ala Xaa Gln Ile Ser Gln Gln
1               5                   10
```

PEPTIDE HAVING CYTOTOXICITY INHIBITORY ACTIVITY AND METHOD OF SCREENING THESE PEPTIDE HAVING CYTOTOXICITY INHIBITORY ACTIVITY

This application is the national phase under 35 U.S.C. §371 of PCT International Application No. PCT/JP02/04557 which has an International filing date of May 10, 2002, which designated the United States of America.

TECHNICAL FIELD OF THE INVENTION

The present invention relates to a protein having a novel function. Specifically, the present invention relates to a selenocysteine-containing peptide fragment having a low toxicity and a cytotoxicity-inhibitory activity. More specifically, the present invention relates to a peptide fragment or a series of peptide fragments having a cytotoxicity-inhibitory activity from selenoprotein P as a preferable embodiment as well as a method for screening molecular species having said activity. The present invention allows for provision of drugs such as a medicament for protecting from exacerbation of conditions of, preventing or treating, various diseases related to cytotoxicity as well as a cosmetics containing molecular species having said activity.

BACKGROUND OF THE INVENTION

It has been suggested that cell death not only plays an important role in basic control of the nervous system, the endocrine system and the immune system in higher organisms but also is deeply involved in many diseases (Thompson C. B., Science, Vol. 267, p. 1456-1462 (1995). Some diseases including, for example, autoimmune diseases such as systemic lupus erythematosus, neurodegenerative diseases due to cytotoxicity, organ transplantation injuries associated with organ transplantation etc. may be regarded as one due to influence of cell death where apoptosis is involved.

Factors causing cytotoxicity includes both an extraneous factor and an intrinsic factor. For an extraneous factor, those of which substantial existence as substance accelerating cytotoxicity have been established include TNF involved in the immune system (Zheng, L., et al., Nature, vol. 377, p. 348-351 (1995)), Fas ligand (Suda T., et al., Cell, vol. 75, p. 1169-1178 (1993)), glucocorticbids (Wyllie A. H., Nature, vol. 284, p. 555-556 (1980)), etc. An extraneous factor also includes lack of a growth factor indispensable to cell growth, such as erythropoietin, interleukins, nerve growth factor, or lack of nutritional factors. In these cases, cytotoxicity is induced by apoptosis caused by change in physiological conditions. Apoptosis may also be induced by non-physiological stresses such as radiation, temperature, anticancer agents, calcium ionophore, active oxygen, etc. In addition, necrosis may also be induced by burn, toxic substance, ischemia, attack by complements, infection with virulent virus, administration of overdose medicaments or overdose radiation.

For an intrinsic factor, there are changes in the metabolic system such as intracellular concentration of $Ca^{2+}$, metabolism of nucleic acids, metabolism of amino acids, metabolism of energy, etc., which lead to cell death. Control of these apoptotic signals could have lead to protection from exacerbation of conditions of, prevention or treatment of, various diseases. However, at present, the mechanism is not so simple that mere control of the causal substance and factors that have hitherto been established cannot afford sufficient clinical application.

On the other hand, as substance that have hitherto been proved to inhibit cytotoxicity, intracellular factors such as bcl-2 and bcl-x are known that are believed to inhibit most of apoptotic signals (Boise L. H., et al., Cell, vol. 74, p. 597-608 (1993)). However, these agents must intracellularly be expressed for causing inhibition of cytotoxicity and effects can hardly be obtained by extracellular addition of these agents. Extracellular factors for inhibiting cytotoxicity have also been reported that inhibit apoptosis by active oxygen, including superoxide dismutase (hereinafter also referred to as "SOD") (Greenlund L. J., et al., Neuron, vol. 14, p. 303-315 (1995)), catalase (Sandstrom P. A. and Buttke T. M., Proc. Natl. Acad. Sci. USA, vol. 90, p. 4708-4712 (1993)), and glutathione peroxidase (Kayanoki Y., et al., J. Biochem., vol. 119, p. 817-822 (1996)). However, cytotoxicity cannot effectively be inhibited by these extracellular factors alone.

DISCLOSURE OF THE INVENTION

While culturing cells, cytotoxicity is induced due to stress to cells imposed by substances from the cultured cells per se or from extraneous additives. However, it is not in all the cells that cytotoxicity is induced under certain conditions. For those cells that survived the circumstances, proteins necessary for suppressing the cytotoxicity-inducing signals due to stress under their thresholds should have already been expressed, or newly induced, either intracellularly or extracellularly. Such proteins include, as envisaged, transcription factor, synthases, enzymes related to metabolism, oxidases, reductases, kinases, transferases, apoptosis-inhibiting proteins, etc. That is, sensitivity to stress in each of respective cells may vary due to difference in their expression level of these proteins. Thus, even if the mechanisms of cytotoxicity are not always the same, if the cytotoxicity-inducing signals could be suppressed under their thresholds by extraneously adding an inhibitory agent to cytotoxicity due to certain stress, then cytotoxicity could possibly be inhibited not only in cultured cells but also within the living body where similar stress occurred.

Cytotoxicity is closely related to diseases. Thus, identification of a number of agents having a cytotoxicity-inhibitory activity within the living body to control a variety of cytotoxicity would not only allow for clinical application such as treatment of diseases but also for application to effective culture of cultured cells. Indeed, although some factors are known that inhibit cytotoxicity, e.g. bcl-2, bcl-x, etc. as intracellular cytotoxicity-inhibitory factors, or SOD, catalase, glutathione peroxidase, etc., as extracellular factors, it is difficult to inhibit cytotoxicity in all types of cells by extracellular addition of these factors. This is due to difference in processes through which cytotoxicity is mediated based on difference in their mechanisms. Taking this into consideration, there is a need to identify activity that significantly, and more specifically, inhibits a variety of cytotoxicity. That is, for the cytotoxicity that is not subject to inhibition by known materials, there is a need to search for factors that can significantly inhibit said cytotoxicity. In addition, cytotoxicity-inhibitory factors are likely to be present for maintaining homeostasis within the living body and hence identification of such factors is extremely significant.

Under the circumstances, the present inventors have found that peptide fragments from the C-terminal of selenoprotein P, a protein from blood components, exhibit a cell death-inhibitory activity, which hitherto has not been reported, and have filed a patent application (PCT/JP99/06322) for this finding. While culturing cells under cell-free conditions or another special conditions, apoptosis induced by stress is frequently observed. In said application, cell culture was performed under these cytotoxicity-inducing conditions and with the index of the cytotoxicity-inhibitory activity novel molecular species having the cytotoxicity-inhibitory activity could be screened by using various chromatographs.

The present inventors further investigated to find some indexes to be used for assessment of said cytotoxicity-inhibitory activity and using said indexes developed a novel method for screening. Using said method for screening, the present inventors found principal regions closely related with the cytotoxicity-in-hibitory activity present in the peptide fragments from the C-terminal of selenoprotein P. Based on this finding, the present inventors have thus completed the present invention.

That is, an object of the present invention is to provide a peptide fragment or a series of peptide fragments with one or more selenocysteine having a lower toxicity than selenocystine and the cytotoxicity-inhibitory activity The peptide fragment or a series of the peptide fragments according to the present invention preferably has the amino acid sequence from 260th to 362nd amino acids from the C-terminal of selenoprotein P, or said amino acid sequence with one or several amino acid residues therein being deleted, substituted or added, or a partial sequence of either of the above amino acid sequences, or an amino acid sequence comprising as a part any of the above amino acid sequences.

More preferably, the peptide fragment or a series of the peptide fragments according to the present invention has the amino acid sequence of the formula: Arg Ser Xaa Cys Cys His Cys Arg His Leu Ile Phe Glu Lys (SEQ ID NO: 1) wherein Xaa represents selenocysteine, or said amino acid sequence with one or several amino acid residues therein being deleted, substituted or added, or a partial sequence of either of the above amino acid sequences, or an amino acid sequence comprising as a part any of the above amino acid sequences.

The present invention further provides a method for screening a substance having the cytotoxicity-inhibitory activity by utilizing a cellular sudden death phenomenon in a cell culture system with serum free culture supplemented with albumin or a fatty acid, which method comprises assessing an extent of cytotoxicity inhibition upon addition of a substance suspected of having the cytotoxicity-inhibitory activity to said cell culture system wherein production of peroxidized lipids is used as an index for assessing an extent of cytotoxicity inhibition.

The present invention also provides a method for screening a substance having the cytotoxicity-inhibitory activity by utilizing a cellular sudden death phenomenon in a cell culture system with serum free culture supplemented with albumin or a fatty acid, which method comprises assessing an extent of cytotoxicity inhibition upon addition of a substance suspected of having the cytotoxicity-inhibitory activity to said cell culture system wherein a glutathione peroxidase (GPX) activity is used as an index for assessing an extent of cytotoxicity inhibition.

BEST MODE FOR CARRYING OUT THE INVENTION

The selenocysteine-containing peptide fragment or a series of peptide fragments having a low toxicity and a cytotoxicity-inhibitory activity as provided by the present invention is a peptide fragment or a series of peptide fragments containing selenium in the form of at least one selenocysteine in the molecule that does not exhibit a significant cytotoxic effect and has a preferable cytotoxicity-inhibitory activity. One embodiment includes a peptide fragment or a series of peptide fragments having a cytotoxicity-inhibitory activity with the amino acid sequence from 260th to 362nd amino acids from the C-terminal of selenoprotein P, or said amino acid sequence with one or several amino acid residues therein being deleted, substituted or added, or a partial sequence of either of the above amino acid sequences, or an amino acid sequence comprising as a part any of the above amino acid sequences, including selenoprotein P as an intact molecule or peptide fragments from the C-terminal of selenoprotein P.

Amino acids comprised of the peptide fragment or a series of the peptide fragments according to the present invention is usually an L-amino acid as in naturally occurring proteins or peptide fragments but may be a D-amino acid.

Selenium per se, as involved in the present invention, is one of essential trace elements and it is known that deficiency thereof induces a serious deficiency disease accompanied by, for instance, cardiomyopathy. It is also demonstrated that selenium is essential for survival, maintenance of life or growth of cells as can be seen from that addition of sodium selenite to culture medium is indispensable during serum-free culture. However, as will be understood from the fact that selenium compounds are designated as poisonous substance, a difference between effective and toxic amounts, i.e. a safety range of concentration, is small and hence selenium compounds used in an excess amount may be toxic to cells to induce unfavorably cell death. Acute toxic symptoms of selenium include, for example, pale face, neurological symptoms, dermatitis, and gastrointestinal disorders. A possibility has been reported that inorganic selenium compounds are also expected to exhibit similar cytotoxicity-inhibitory activity to that of the peptide fragment of the present invention (B. Chem. J. (1998) vol. 232, p. 231-236). However, these substances exhibit strong toxicity and hence the activity not accompanied by toxicity is needed.

In the living body, selenium is incorporated into proteins primarily in the form of selenocysteine. Selenocystine, a dimer of selenocysteine, exhibits fairly strong toxicity when added alone to cell culture. On the contrary, no strong toxicity was observed in selenoprotein P or a peptide fragment from the C-terminal of selenoprotein P, as a preferable embodiment of the present invention, in spite of the presence of 9 to 10 selenocysteine residues therein. This suggests that inclusion of said amino acids in a peptide fragment is indispensable for decreasing toxicity of selenoprotein P. In fact, selenocysteine-containing synthetic peptides comprising 4 to 14 amino acid residues exhibited no toxicity at a concentration where selenocystine exhibited toxicity.

The peptide fragment or a series of the peptide fragments of the present invention not only allows for providing selenium compounds that have reduced toxicity but also provides an unexpected cytotoxicity-inhibitory activity.

In PCT/JP99/06322, the prior application to the instant application, the following method for screening the activity was used.

For screening factors having the cytotoxicity-inhibitory activity, a culture system first needs be established where cytotoxicity is induced. As one of preferable embodiments, a culture system of Dami cells, human megakaryoblasts, with serum free culture medium supplemented with albumin was used for screening. Dami cells may be subcultured on a mixed culture medium of RPMI 1640, D-MEM and F-12 (1:2:2) supplemented with 0.1% BSA and 0.05 μM 2-mercaptoethanol but can hardly grow on albumin-deprived medium. With culture medium containing 0.01 to 0.5% human serum albumin, the cells grow normally but are put to death on Day 4 abruptly not gradually. A diluted sample of active fractions was added to this culture system so that the cytotoxicity-inhibitory activity could be assessed.

The present inventors further found that a fatty acid played a role in cytotoxicity induction and attempted to add a fatty acid instead of albumin described above to the cell culture system.

Any long-chain fatty acid with at least two double bonds including, for example, eicosadienoic acid, dihomo-γ-linolenic acid, docosadienoic acid, docosatrienoic acid, adrenic acid, eicosapentaenoic acid, docosahexaenoic acid, linoleic acid, linolenic acid and arachidonic acid induced cytotoxicity at 10 μM in serum free culture in the absence of molecular species having the cytotoxicity-inhibitory activity such as peptide fragments from selenoprotein P.

With the cultured cells used in the foregoing assessment system, the present inventors have focused on "production of peroxidized lipids" in the culture cell system that was closely related to cytotoxicity and "intracellular GPX (glutathione peroxidase) activity" that inhibited cytotoxicity, and, by using these two as an index, established a method for screening molecular species having the cytotoxicity activity.

The first index is accumulation of peroxidized lipids in the assessment system. When a long-chain fatty acid was added to the cell culture system, cytotoxicity was induced and a level of peroxidized lipids was extremely increased. On the contrary, when molecular species having the cytotoxicity-inhibitory activity was added to the same system, cytotoxicity was inhibited and simultaneously increase in a level of peroxidized lipids was inhibited.

Secondly, an intracellular GPX activity in the assessment system is used as an index. GPX is responsible for an intracellular anti-oxidative activity and its level is closely related, and is negatively correlated, with cytotoxicity. This phenomenon can be used in the assessment system for the cytotoxicity-inhibitory activity.

The present inventors could use the assessment system as described above for the cytotoxicity with the indexes as described above to find out principal regions closely related with the cytotoxicity-inhibitory activity present in the peptide fragments from the C-terminal of selenoprotein P.

The present inventors confirmed in a preliminary experiment that peptide fragments with amino acid sequences starting from the 260th amino acid in the C-terminal of. selenoprotein P had the cytotoxicity-inhibitory activity and based on this finding, further continued investigation. As a result, the present inventors have found that a peptide fragment or a series of peptide fragments with the amino acid sequence from 260th to 362nd amino acids from the C-terminal of selenoprotein P had an excellent cytotoxicity-inhibitory activity. Said peptide fragment or a series of peptide fragments encompasses those with said amino acid sequence with one or several amino acid residues therein being deleted, substituted or added, or with a partial sequence of either of the above amino acid sequences, or with an amino acid sequence comprising as a part any of the above amino acid sequences, in addition to the amino acid sequence of naturally occurring selenoprotein P. That is, the peptide fragment or a series of the peptide fragments of the present invention includes any molecular type without any restriction as far as it derives from the C-terminal of selenoprotein P and exhibits the cytotoxicity-inhibitory activity. A preferable embodiment of the peptide fragment of the present invention includes, among the peptide fragments from the C-terminal of selenoprotein P, in particular a peptide fragment with the amino acid sequence from 279th to 292nd amino acids from the C-terminal of selenoprotein P wherein Cys is replaced with Ser, which exhibits an excellent cytotoxicity-inhibitory activity. The peptide fragments of the present invention obtained on the basis of the finding as described above may be prepared by the conventional methods using a peptide synthesizer. Alternatively, chemical compounds may also be designed by using the peptide fragments of the present invention as a lead substance.

It is reported that in general a free fatty acid level is raised by as much as more than three times to bring about cytotoxic effect at the time when the living body is subject to a certain stress such as hemostasis, occurrence of inflammation, disorder in organs, damage in cells, damage in blood vessels, bacterial infection, viral infection, etc. ("Chemistry of Lipids", p. 170-179, ed. by Haruo Nakamura, Asakura Shoten (1990); "Handbook of Cerebral Apoplexy Experiment", p. 437-471, supervised by Keiji Sano, IPC (1990)). From this teaching, it is anticipated that cells are adversely effected by a fatty acid under circumstances where stressful state is maintained though sensitivity may vary depending on the types of cells. That is, against stress that may be encountered while operation, i.e. hemorrhage, hemostasis or ischemia, stress of reperfusion after ischemia associated with diseases or organ transplantation, or stress by continuous inflammation, the active peptide fragment or a series of the peptide fragments of the present invention from selenoprotein P can reduce adverse effects by a fatty acid or prevent exacerbation of conditions by enhancing antioxidant activity of cells. The active peptide fragment or a series of the peptide fragments of the present invention would also serve as stabilizing cells by enhancing antioxidant ability of cells against any phenomena where oxidation stress of cells is raised through the similar mechanism.

It is anticipated that the active peptide fragment or a series of the peptide fragments of the present invention function within the living body in the activated form after processing for protecting cells from stress-derived cytotoxicity and for stabilizing cells. That is, when too much stress is burdened to such a degree that the living body is no more durable thereto, cytotoxicity could have occurred. Thus, in such a case, if the active peptide fragment or a series of the peptide fragments of the present invention could be supplied extraneously, it would be possible to prevent from progressing into severe diseases or to treat diseases. Specifically, diseases induced and effected by oxidation stress include AIDS, Parkinson's disease, Alzheimer's disease, etc. and the active peptide fragment or a series of the peptide fragments of the present invention is likely to ameliorate these diseases. Besides, since it is found that oxidized LDL is involved in onset of arteriosclerosis as a causing factor, application for protection from exacerbation of conditions, prevention or treatment of arteriosclerosis is also envisaged. It is also efficacious to diseases in which reperfusion injury is observed such as myocardial infarction, cerebral infarction or organ transplantation. In addition, it is demonstrated that the active peptide fragment or a series of the peptide fragments efficiently work in culture of B cells and T cells. Thus, they may also be used as an immunostimulatory or immunoregulatory agent through stabilization or regulation of cells of the immune system. Besides, in addition to application to a medical drug, they may also be used as a component in cosmetics capable of reducing stress due to unbalance in oxidative-reductive conditions in cells or sunburn etc. Moreover, they may also be used for enhancing efficiency of culture conditions, for example, in case of production of useful biological substances, by preventing cytotoxicity due to excessive stress while cell culture.

In fact, the present inventors proved that the cysteine-containing peptide fragment or a series of the peptide fragments of the present invention was useful as a promising inhibitor to ischemia-reperfusion injury where cytotoxicity is deeply involved using cerebral ischemia-reperfusion injury animal model.

The present invention is explained in more detail by means of the following Examples which are not intended to restrict a scope of the present invention in any sense. Reagents used in the following Examples were obtained from Wako Pure Chemical Industries, Ltd., TAKARA SHUZO CO., Ltd., Toyobo, and New England BioLabs.

Preparation (Purification of Components Having Cell Death-Inhibitory Activity from Human Plasma)

In the following purification procedure, the activity was assessed in accordance with the assay procedure described in Reference Example 1.

The cell death-inhibitory activity in plasma shows heparin-binding activity. Thus, fractionation with a heparin column was initially performed for collecting heparin-binding fractions from plasma. Using human plasma as starting material, heparin-binding proteins in plasma were adsorbed to a heparin column (Heparin Sepharose: manufactured by Pharmacia). After washing with 0.3 M sodium chloride, the adsorbed fractions were eluted with 2 M sodium chloride. Although most of the cell death-inhibitory activity of interest was recovered in the fractions after washing with 0.3 M sodium chloride, the fractions eluted with 2 M sodium chloride were used for purification of active substance.

For crude fractionation of the heparin-bound cell death-inhibitory activity, fractionation with ammonium sulfate precipitation was performed. To the heparin-binding fractions eluted with 2 M sodium chloride was added ammonium sulfate in an amount of 31.3% W/V (about 2 M) based on a total amount of the fractions and precipitates were recovered. The precipitates were dissolved in water and dialyzed against water with a dialysis membrane of M.W. 3,500 cut. After completion of dialysis, the solution was recovered and 1 M Tris-HCl buffer, pH 8.0 was added thereto in an amount of 1/50 volume based on a total of the solution. A concentration of the solution was adjusted with 20 mM Tris-HCl buffer, pH 8.0 so that 20 to 30 of OD280 value was obtained. The solution was filtrated with 1.0 μm and 0.45 μm filters for removal of impurities.

An anion exchange chromatography was performed by passing the proteinaceous solution after filtration through anion exchange chromatographic carrier (Macro-prep High Q: manufactured by BioRad) equilibrated with 20 mM Tris-HCl buffer, pH 8.0. The activity was detected in non-adsorbed fractions and fractions eluted with 50 mM sodium chloride, which were collected. To the active fractions obtained by anion exchange chromatography was added a 6:4 mixture of 1 M citrate buffer, pH 4.0 and 1 M citric acid in an amount of 1/50 volume based on a total of the fractions so that a proteinaceous solution was obtained as 20 mM citrate buffer, pH about 4.0.

A cation exchange chromatography was performed by passing the proteinaceous solution through cation exchange chromatographic carrier (Macro-prep High S: manufactured by BioRad) equilibrated with 20 mM citrate buffer, pH 4.0. The column was washed with 20 mM citrate buffer, pH 4.0 containing 220 mM sodium chloride. The activity was detected in fractions eluted with 20 mM citrate buffer, pH 4.0 containing 550 mM sodium chloride, which were collected.

To the fractions eluted with 550 mM sodium chloride was added 1 M Tris-Aminomethane solution in an amount of 1/30 volume based on a total of the fractions and pH was adjusted to about 7.5. To this solution was added a 3.5 M ammonium sulfate solution (pH was adjusted to about 7.5 by adding 1 M Tris-HCl buffer, pH 8.5 in an amount of 1/50 volume) in an amount of 2/3 volume. Then, a salt concentration was adjusted so that 1.4 M ammonium sulfate and 330 mM sodium chloride concentrations were obtained. The solution was filtrated with 0.45 μm filter for removal of impurities.

Figure 1:
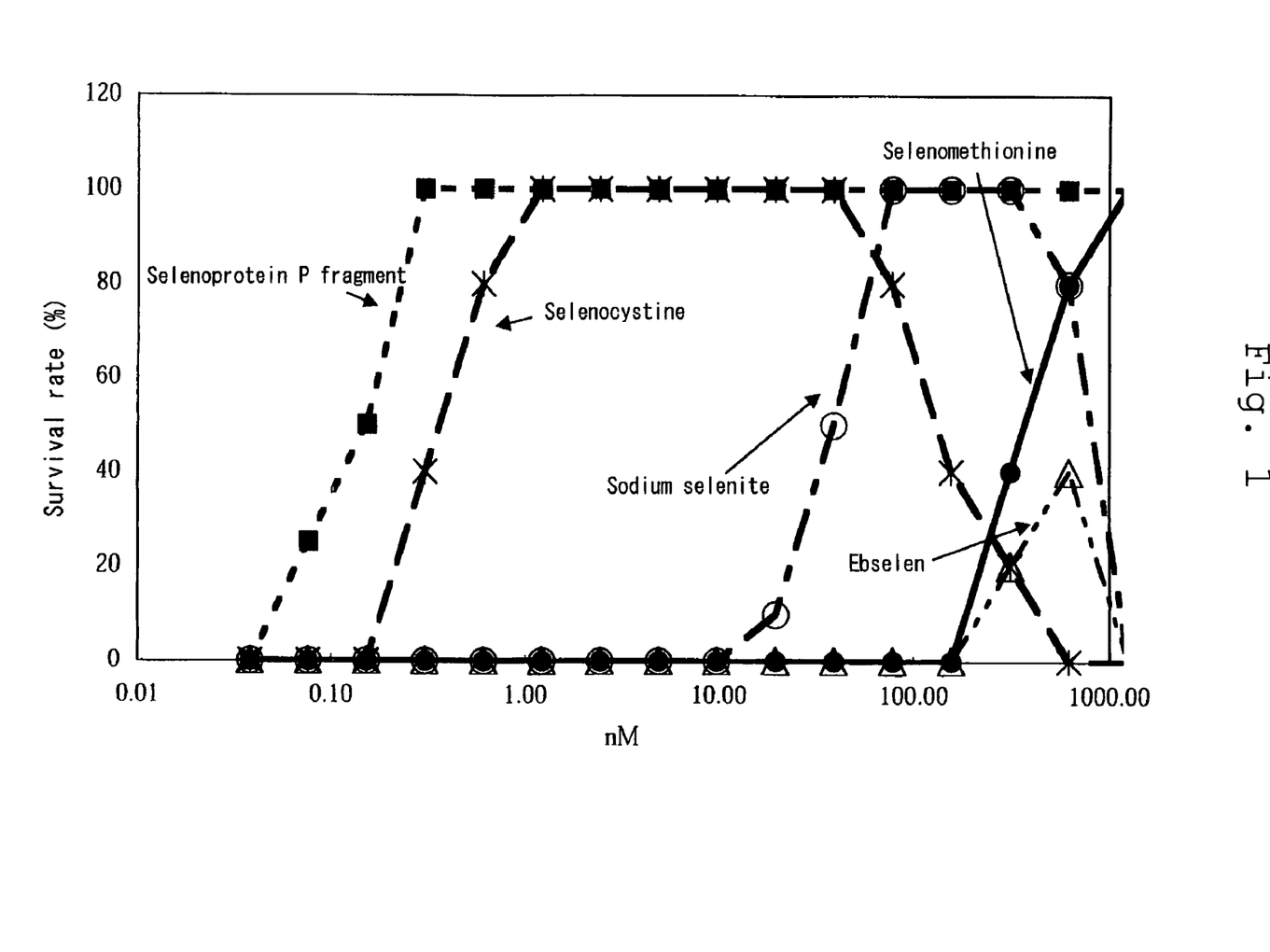
FIG. 1 shows results of determination of the cytotoxicity-inhibitory activity and a minimum concentration of the cytotoxic effect of the peptide fragment of the present invention and various other samples.

A hydrophobic chromatography was then performed by passing the proteinaceous solution after filtration through hydrophobic chromatographic carrier (Macro-prep Methyl HIC: manufactured by BioRad) equilibrated with 20 mM Tris-HCl buffer, pH 7.5 containing 1.4 M ammonium sulfate and 330 mM sodium chloride. The activity was detected in non-adsorbed fractions and fractions eluted with the buffer for equilibration, pH 7.5, which were collected. The activity could hardly be detected in the adsorbed fractions. For the purpose of rendering the active fractions be adsorbed onto the hydrophobic chromatographic carrier, to the active fractions was added the 3.5 M ammonium sulfate solution, pH about 7.5 so that 2.0 M of an ammonium sulfate concentration was obtained. The sample was passed through hydrophobic chromatographic carrier (Macro-prep Methyl HIC: manufactured by BioRad) equilibrated with 20 mM Tris-HCl buffer, pH 7.5 containing 2.0 M ammonium sulfate and 240 mM sodium chloride to render the active components be adsorbed. After washing with the buffer for equilibration, the adsorbed active components were eluted with 20 mM Tris-HCl buffer, pH 8.0. The recovered active fractions were dialyzed against water overnight. For ensuring adsorption of the active fractions onto heparin column, 1 M citrate buffer, pH 4.5 was added to the recovered active fractions in an amount of 1/50 volume to adjust pH about 5.0. Up to this procedure, see FIG. 1.

A 20 mM phosphate buffer, pH 6.5 ("Buffer A") and a 20 mM phosphate buffer, pH 6.2 containing 2 M sodium chloride ("Buffer B") were prepared. The pH adjusted, active fractions were passed through heparin column (Hi-Trap Heparin: manufactured by Pharmacia) equilibrated with Buffer A. The column was washed with a twice volume of a 5% mixture of Buffer B in Buffer A (0.1 M NaCl). The active fraction was eluted with a 20% mixture of Buffer B in Buffer A (0.4 M NaCl) and recovered. The thus obtained active fraction was concentrated to about 15 mg/ml with a membrane concentrator (Centriprep 3: manufactured by Amicon). To the concentrated active fraction was added 2% acetic acid based on a total of the fraction and then impurities were removed with 0.45 μm filter.

Gel filtration chromatography was performed by passing 1 ml of the active fraction through gel filtration chromatographic carrier (Superdex 200pg: manufactured by Pharmacia) equilibrated with a solution containing 2% acetic acid and 500 mM sodium chloride. After fractionation, the active fraction was recovered.

The above fraction was passed through C4 reverse phase HPLC (Wakosil 5C4-200: 6 mm×150 mm: manufactured by Wako Jun-yaku K.K.) equilibrated with 1% acetonitrile containing 0.1% trifluoroacetic acid and 1% isopropanol. The column was washed with the buffer used for equilibration. A linear gradient elution with 1% to 40% acetonitrile containing 0.1% trifluoroacetic acid and 1% isopropanol was then performed and the obtained active fractions were recovered. The progress of the activity and the specific activity obtained in each of the above purification procedures is summarized in Table 1 below.

TABLE 1

| Purification Step | Conc. of Protein (mg/ml) | Activity | Specific Activity |
|---|---|---|---|
| (1) | 64 | 2,400 | 38 |
| (2) | 22.6 | 12,800 | 566 |
| (3) | 2.1 | 4,800 | 2,286 |
| (4) | 0.4 | 1,600 | 4,000 |
| (5) | 2.8 | 12,800 | 4,571 |
| (6) | 6.8 | 25,600 | 3,765 |
| (7) | 1.6 | 25,600 | 16,000 |
| (8) | 0.9 | 204,800 | 227,556 |

(1): Starting plasma
(2): Heparin elution/treatment with ammonium sulfate
(3): Anion exchange chromatography; non-adsorbed fraction
(4): Anion exchange chromatography; adsorption and elution
(5): Cation exchange chromatography; adsorption and elution
(6): Hydrophobic chromatography; adsorption and elution
(7): HiTrap heparin, adsorption and elution
(8): C4 Reverse phase HPLC For fractionating the obtained active fraction more fully, fractionation was further performed using ion exchange chromatographic carrier Mini Q (manufactured by Pharmacia). A linear gradient elution with sodium chloride was carried out under the condition of 20 mM ethanolamine, pH 9.15. The activity was detected in all the fractions obtained.

REFERENCE EXAMPLE 1

(Assessment System for Activity to Inhibit Cytotoxicity Induced by Addition of Albumin)

To 1 ml Dami cells (described in Greenberg S. M. et al., Blood, vol. 72, p. 1968-1977 (1988); $1 \times 10^6$ cells/dish/3 ml), which can be subcultured in serum free medium SFO3 (manufactured by Sanko Jun-yaku K.K.) containing 0.05 µM 2ME and 0.1% BSA, was added 2 ml 1:2:2 mixed medium (SA medium) of RPMI 1640/D-MEM/F-12. The cells were cultured for three days and recovered for assay. The cells were washed twice with 50% PBS/SA/0.03% HSA (manufactured by SIGMA) and suspended in the same medium at $3 \times 10^4$ cells/ml. The cell suspension was added to a 96-well plate in each 200 µl for wells for sample addition or in each 100 µl for wells for serial dilution. To the wells for sample addition was added 2 µl assay sample and, after stirring, a serial dilution was made with the wells containing 100 µl cell suspension. The plate was incubated at 37° C. in $CO_2$ incubator for 4 to 5 days followed by assessment.

For assessment, it was examined to what folds of dilution of tested samples the cells could survive in view of the fact that on Day 4 the cells in wells without the activity were put to death whereas the cells in wells with the activity survived.

REFERENCE EXAMPLE 2

(Cytotoxicity Induced by Fatty Acid and Inhibitory Activity Thereto)

Any long-chain fatty acid with at least two double bonds including, for example, eicosadienoic acid, dihomo-γ-linolenic acid, docosadienoic acid, docosatrienoic acid, adrenic acid, eicosapentaenoic acid, docosahexaenoic acid, linoleic acid, linolenic acid and arachidonic acid induced cytotoxicity at 10 µM in serum free culture in the absence of selenoprotein P. Among these, the most potent cytotoxicity inducer, arachidonic acid, linoleic acid and linolenic acid were thoroughly investigated for their concentration that induced cytotoxicity as well as a concentration of selenoprotein P necessary for inhibiting the cytotoxicity.

To 1 ml Dami cells ($1 \times 10^6$ cells/dish/3 ml), which can be subcultured in serum free medium SFO3 (manufactured by Sanko Jun-yaku K.K.) containing 0.05 µM 2ME and 0.1% BSA, was added 2 ml 1:2:2 mixed medium (SA medium) of RPMI 1640/D-MEM/F-12. The cells were cultured for three days and recovered for assay. The cells were washed twice with SA/0.05% fatty acid free BSA (manufactured by Wako Jun-yaku K.K.) and suspended at $3 \times 10^4$ cells/ml in the same medium containing 2 to 16 µM arachidonic acid, linoleic acid or linolenic acid. The cell suspension was added to a 96-well plate in each 198 µl for wells for sample addition or in each 100 µl for wells for serial dilution.

To the wells for sample addition was added each 2 µl of 100 µM assay sample and, after stirring, a serial dilution was made with the wells containing 100 µl cell suspension. The plate was incubated at 37° C. in $CO_2$ incubator for 4 to 5 days. Cytotoxicity induction and inhibition of cytotoxicity by selenoprotein P fragment were assessed with 1 µM selenoprotein P fragment and effective concentration thereof by serial dilution.

It was demonstrated that cytotoxicity was induced in serum free culture of the cells in the presence of 4 µM or more multivalent unsaturated fatty acids such as arachidonic acid or linoleic acid and was completely inhibited by 1 µM selenoprotein P fragment. As compared to vitamin E which inhibited cytotoxicity in the presence of 4 µM linoleic acid at an effective concentration of about 100 nM, a full-length selenoprotein P and a peptide fragment from selenoprotein inhibited at an effective concentration of about 100 nM and 10 µM, respectively. Thus, the peptide fragment from selenoprotein could inhibit cytotoxicity at much lower effective concentration. From the fact that vitamin E, an antioxidant, did inhibit cytotoxicity, it was estimated that fatty acids, upon being peroxidized either intracellularly or extracellularly, damaged cells leading to cytotoxicity whereas the peptide fragment from selenoprotein P efficiently prevented these events from occurring.

Then, various enzymes related to oxidation/reduction were investigated for their activity to inhibit cytotoxicity induced in Dami cells in the presence of 4 µM linoleic acid or linolenic acid. The enzymes tested include glutathione peroxidase, superoxide dismutase, glutathione reductase, glutathione-S-transferase, and catalase. Only glutathione peroxidase could inhibit cytotoxicity at 250 nM or more in the presence of linoleic acid and at 500 nM or more in the presence of linolenic acid. The other enzymes, however, could not inhibit cytotoxicity even at 1 µM or more. The fact that the selenoprotein P fragment could inhibit cytotoxicity at as low as 10 µM in the same assay condition proved prominent efficacy of the selenoprotein P fragment. By varying a concentration of fatty acids in induction of cytotoxicity, influence of fatty acids to various types of cells with different sensitivity or influence of selenoprotein P thereto could be observed. Usually, cytotoxicity is induced by the addition of 20 µM linoleic acid and, if cytotoxicity is not induced by this condition, selenoprotein P is likely to be expressed. Using this system, the inhibitory activity to cytotoxicity induced by fatty acids can be assessed in various types of cells. This system was considered to reflect the similar events to cytotoxicity induced by adding HSA (SIGMA).

Hitherto, the selenoprotein P fragment was proved to be effective in megakaryoblasts cell lines (Dami), T cell-derived cell lines (Molt4, CEM, Jurkat), B cell-derived cell lines (P3X63AG8.653, P3X63AG8.U1), liver-derived cell lines (HepG2), nervous system-derived cell lines (IMR 32), kidney-derived cell lines (CRL 1932), etc. Thus, it was highly expected that the selenoprotein P fragment could also exert cytotoxicity-inhibitory activity to the cells from the immune system, the nervous-system or the hemopoietic system, or from the organs.

EXAMPLE 1

(Peptide Synthesis)

Selenocysteine was protected with Fmoc (9-Fluorenylmethoxycarbonyl) or MBzl (p-Methoxybenzyl). With the protected selenocysteine, desired peptides were synthesized by the Fmoc technique with a peptide synthesizer. Then, the peptides were deprotected and purified by reverse phase HPLC.

The present inventors confirmed that a peptide fragment having the amino acid sequence: Lys Arg Cys Ile Asn Gln Leu Leu Cys Lys Leu Pro Thr Asp Ser Glu Leu Ala Pro Arg Ser Xaa Cys Cys His Cys Arg His Leu Ile Phe Glu Lys (SEQ ID NO: 3) wherein Xaa represents selenocysteine had the cytotoxicity-inhibitory activity, which peptide fragment was purified under reduced condition from selenoprotein P fragment having the amino acid sequence: 260Lys Arg Cys Ile Asn Gln Leu Leu Cys Lys Leu Pro Thr Asp Ser Glu Leu Ala Pro Arg Ser Xaa Cys Cys His Cys Arg His Leu Ile Phe Glu Lys Thr Gly Ser Ala Ile Thr Xaa Gln Cys Lys Glu Asn Leu Pro Ser Leu Cys Ser Xaa Gln Gly Leu Arg Ala Glu Glu Asn Ile Thr Glu Ser Cys Gln Xaa Arg Leu Pro Pro Ala Ala Xaa Gln Ile Ser Gln Gln Leu Ile Pro Thr Glu Ala Ser Ala Ser Xaa Arg Xaa Lys Asn Gln Ala Lys Lys Xaa Glu Xaa Pro Ser Asn362 (SEQ ID NO: 2) wherein Xaa is as defined above, having the cytotoxicity-inhibitory activity. Based on this, peptides having the amino acid sequences as described below were synthesized.

TABLE 2

Peptide 1:

Lys Arg Cys Ile Asn Gln Leu Leu    (SEQ ID NO: 4)
Cys Lys Leu Pro Thr Asp Ser Glu
Leu Ala Pro Arg Ser

Peptide 2:

Arg Ser Ser Cys Cys His Cys Arg    (SEQ ID NO: 5)
His Leu Ile Phe Glu Lys

Peptide 3:

Arg Ser Xaa Cys Cys His Cys Arg    (SEQ ID NO: 1)
His Leu Ile Phe Glu Lys

Peptide 4:

Arg Ser Xaa Ser Cys His Cys Arg    (SEQ ID NO: 6)
His Leu Ile Phe Glu Lys

TABLE 2-continued

Peptide 5:

Arg Ser Xaa Ser Ser His Cys Arg    (SEQ ID NO: 7)
His Leu Ile Phe Glu Lys

Peptide 6:

Arg Ser Xaa Ser Ser His Ser Arg    (SEQ ID NO: 8)
His Leu Ile Phe Glu Lys

Peptide 7:

Arg Ser Xaa Ser                    (SEQ ID NO: 9)

Peptide 8:

Thr Gly Ser Ala Ile Thr Xaa Gln    (SEQ ID NO: 10)
Ser Lys

Peptide 9:

Glu Asn Leu Pro Ser Leu Ser Ser    (SEQ ID NO: 11)
Xaa Gln Gly Leu Arg

Peptide 10:

Ala Glu Glu Asn Ile Thr Glu Ser    (SEQ ID NO: 12)
Ser Gln Xaa Arg

Peptide 11:

Leu Ile Pro Thr Glu Ala Ser Ala    (SEQ ID NO: 13)
Ser Xaa Arg

Peptide 12:

Lys Asn Gln Ala Lys Lys Xaa Glu    (SEQ ID NO: 14)

Peptide 13:

Xaa Pro Ser Asn                    (SEQ ID NO: 15)

Peptide 14:

Lys Glu Phe Ile Leu His Arg Ser    (SEQ ID NO: 16)
His Ser Ser Xaa Ser Arg

Peptide 15:

Ser Xaa Ser

Peptide 16:

Leu Pro Pro Ala Ala Xaa Gln Ile    (SEQ ID NO: 17)
Ser Gln Gln

[The amino acid sequence of peptide 14 corresponds to the amino acid sequence of peptide 6 in the direction from the C-terminal to the N-terminal thereof.]

EXAMPLE 2

(Minimum Concentration for Cytotoxic Effect)

Using Dami cells (described in Greenberg S. M. et al., Blood, vol. 72, p. 1968-1977 (1988)) for use in assay system for the cytotoxicity-inhibitory activity, the cells were washed twice with assay medium (50% PBS/SA/0.03% HSA (manufactured by SIGMA) or SA/0.05% BSA free from fatty acid (WAKO)/4 µM long-chain polyvalent fatty acid (e.g. arachidonic acid, linoleic acid or linolenic acid)) and suspended in the same medium at $3 \times 10^4$ cells/ml. The cell suspension was added to a 96-well plate in each 200 µl for wells for sample addition or in each 100 µl for wells for serial dilution. To the wells for sample addition was added each 2 µl assay sample containing either the peptides synthesized in Example 1, selenocystine, selenomethionine, Ebselen, or sodium selenite at the same concentration. After stirring, a serial dilution was made with the wells containing 100 μl cell suspension. The plate was incubated at 37° C. in CO$_2$ incubator for 4 to 5 days followed by assessment of survival of the cells.

After initiation of culture, cells in the wells where toxicity is present will either die or significantly decrease in their number whereas those in the wells where cytotoxicity-inhibitory activity exceeds toxicity will continue to survive with the cell number being substantially maintained. Thus, assessment of toxicity was made by comparing these two types of the wells to determine a concentration that exhibited toxicity. Toxicity was observed with selenocystine and Ebselen at around 200 nM or sodium selenite at around 500 nM on the basis of a selenium concentration contained therein. On the contrary, no toxicity was observed with selenoprotein P fragment, selenomethionine and the selenocysteine-containing peptide fragment even at 1 μM or more. An effective minimum concentration of selenium to inhibit 80% or more of cytotoxicity is 200 to 500 μM for selenoprotein P fragment, around 500 μM to 1 nM for the synthetic peptide No. 6, and around 1 μM for selenomethionine. Even Ebselen, considered to show comparatively low toxicity, exhibited a strong toxicity upon addition to the culture cells and hence proved not be efficacious.

As a result, it were selenoprotein P fragment and the synthetic peptide that were confirmed efficacious with low toxicity. See FIG. 1.

EXAMPLE 3

(Screening of Efficacious Peptides)

Figure 2:
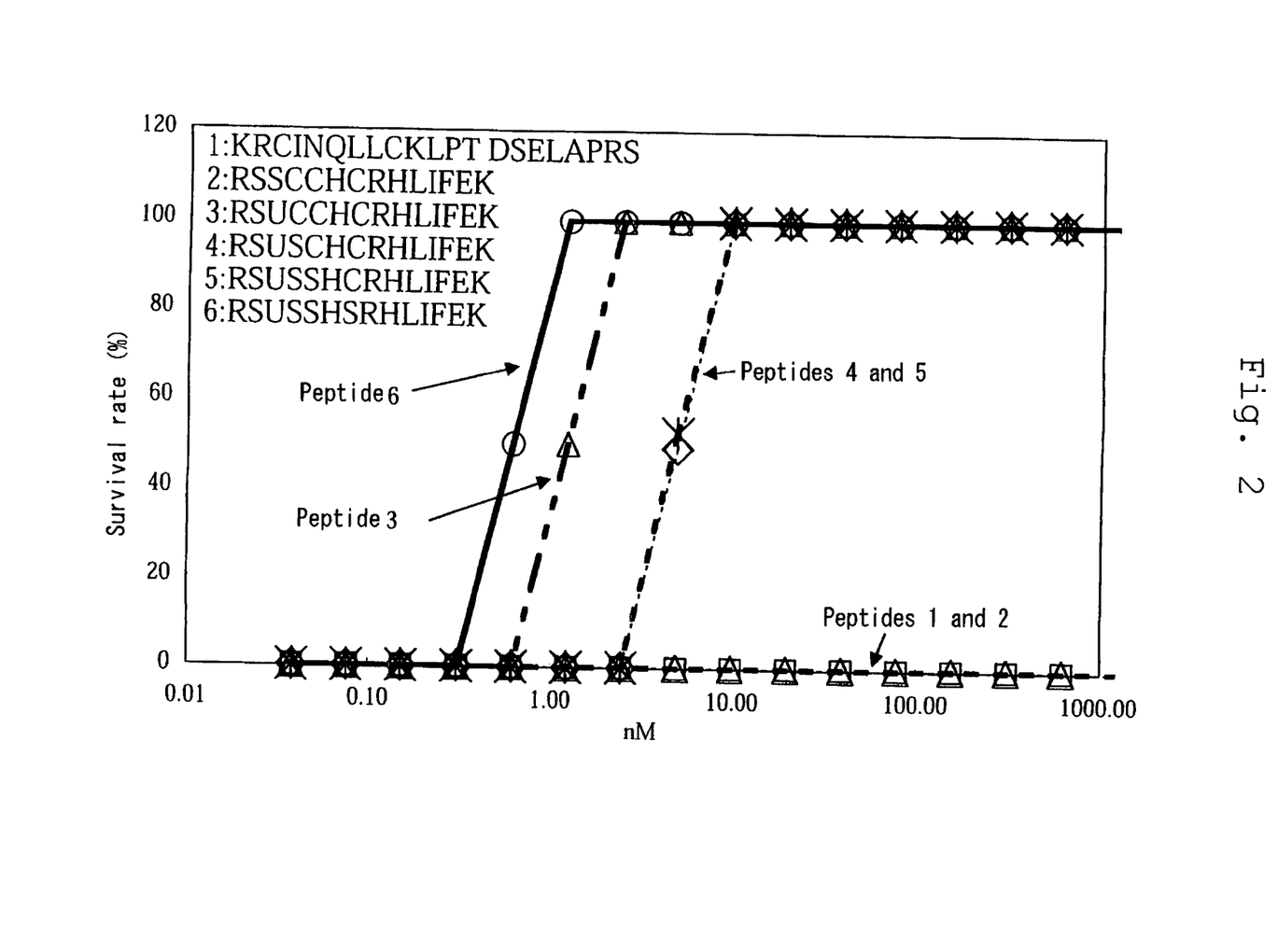
FIG. 2 shows results of determination of the cytotoxicity-inhibitory activity of the peptide fragment of the present invention.

Cytotoxicity-inhibitory activity was determined for each of the peptides obtained above as described in Reference Example 1 and in accordance with Reference Example 2. As a result, selenocysteine-containing peptides, Peptide 3 through Peptide 16, were confirmed to have the cytotoxicity-inhibitory activity. Among these, Peptide 6, in which Cys residues were all replaced with Ser, could inhibit cytotoxicity most effectively at the lowest concentration. Although, any selenium-containing substance exhibited cytotoxicity-inhibitory activity, peptide bond-containing selenocysteine showed apparently lowered toxicity. Thus, it was found that such a peptide fragment that lowered the cytotoxic effect and exhibited efficacious cytotoxicity-inhibitory activity could be screened by the method described herein. See FIG. 2 and Table 3.

TABLE 3

| Peptide | Amino acid sequence | | Activity/1 mM Sec |
|---|---|---|---|
| Peptide 1: | KRCINQLLCKLPTDSELAPRS | (SEQ ID NO: 4) | 0 |
| Peptide 2: | RSSCCHCRHLIFEK | (SEQ ID NO: 5) | 0 |
| Peptide 3: | RSUCCHCRHLIFEK | (SEQ ID NO: 1) | 95,000 |
| Peptide 4: | RSUSCHCRHLIFEK | (SEQ ID NO: 6) | 24,000 |
| Peptide 5: | RSUSSHCRHLIFEK | (SEQ ID NO: 7) | 16,000 |
| Peptide 6: | RSUSSHSRHLIFEK | (SEQ ID NO: 8) | 395,000 |
| Peptide 7: | RSUS | (SEQ ID NO: 9) | 95,000 |
| Peptide 8: | TGSAITUQSK | (SEQ ID NO: 10) | 79,000 |
| Peptide 9: | ENLPSLSSUQGLR | (SEQ ID NO: 11) | 24,000 |
| Peptide 10: | AEENITESSQUR | (SEQ ID NO: 12) | 6,000 |
| Peptide 11: | LIPTEASASUR | (SEQ ID NO: 13) | 28,000 |
| Peptide 12: | KNQAKKUE | (SEQ ID NO: 14) | 24,000 |
| Peptide 13: | UPSN | (SEQ ID NO: 15) | 24,000 |
| Peptide 14: | KEFILHRSHSSUSR | (SEQ ID NO: 16) | 95,000 |
| Peptide 15: | SUS | | 95,000 |
| Peptide 16: | LPPAAUQISQQ | (SEQ ID NO: 17) | 24,000 |
| Purified selenoprotein P fragment | | | 470,000 |

[In the amino acid sequence shown in Table 1, "U" represents selenocysteine.]

EXAMPLE 4

(Activity to Inhibit Production of Peroxidized Lipids)

Assuming accumulation of peroxidized lipids as a possible causative agent of cytotoxicity, an intracellular level of peroxidized lipids was measured with an assay kit in order to investigate if a peroxidized lipid level within cells cultured in the presence of linoleic acid is altered with or without selenoprotein P fragments. Since there can not be denied the possibility that the peroxidized lipid level in the cells with cytotoxicity was increased due to spontaneous oxidation, cytotoxicity was also induced by UV radiation or by being left to stand at room temperature and a production rate of peroxidized lipids was compared with that of cytotoxicity induced by linoleic acid.

Dami cells cultured in SA(−) were centrifuged, recovered and washed and then resuspended in SA(−) at 2.5×10$^5$ cells/ml. Each 20 ml of the suspension was delivered into six 15 cm dishes and 10% BSA mixed with linoleic acid at 1 mg/ml was added to four dishes at 0.05% BSA(−). Among the four dishes to which linoleic acid was added, the two dishes were added with 2.5 mg/ml of a selenoprotein P fragment (50 µl) and incubated at 37° C. for 16 hours. The six dishes were collected and an amount of peroxidized lipids was measured with Lipid hydroxide assay kit (Cyman).

Separately, in order to investigate cytotoxicity caused by UV radiation, Dami cells cultured in SA(−) were centrifuged, recovered and washed and then resuspended in SA(−) at $2.5 \times 10^5$ cells/ml. Each 20 ml of the suspension was delivered into two 15 cm dishes, which were subject to UV radiation for 15 minutes and incubated at 37° C. for 16 hours. The two dishes were collected and an amount of peroxidized lipids was measured with Lipid hydroxide assay kit (Cyman).

Similarly, in order to investigate cytotoxicity caused by being left at room temperature, Dami cells cultured in SA(−) were centrifuged, recovered and washed and then resuspended in SA(−) at $2.5 \times 10^5$ cells/ml. The suspension (20 ml) was delivered into a 15 cm dish, which was left to stand at room temperature for 24 hours. The dish was collected and an amount of peroxidized lipids was measured with Lipid hydroxide assay kit (Cyman).

Figure 3:
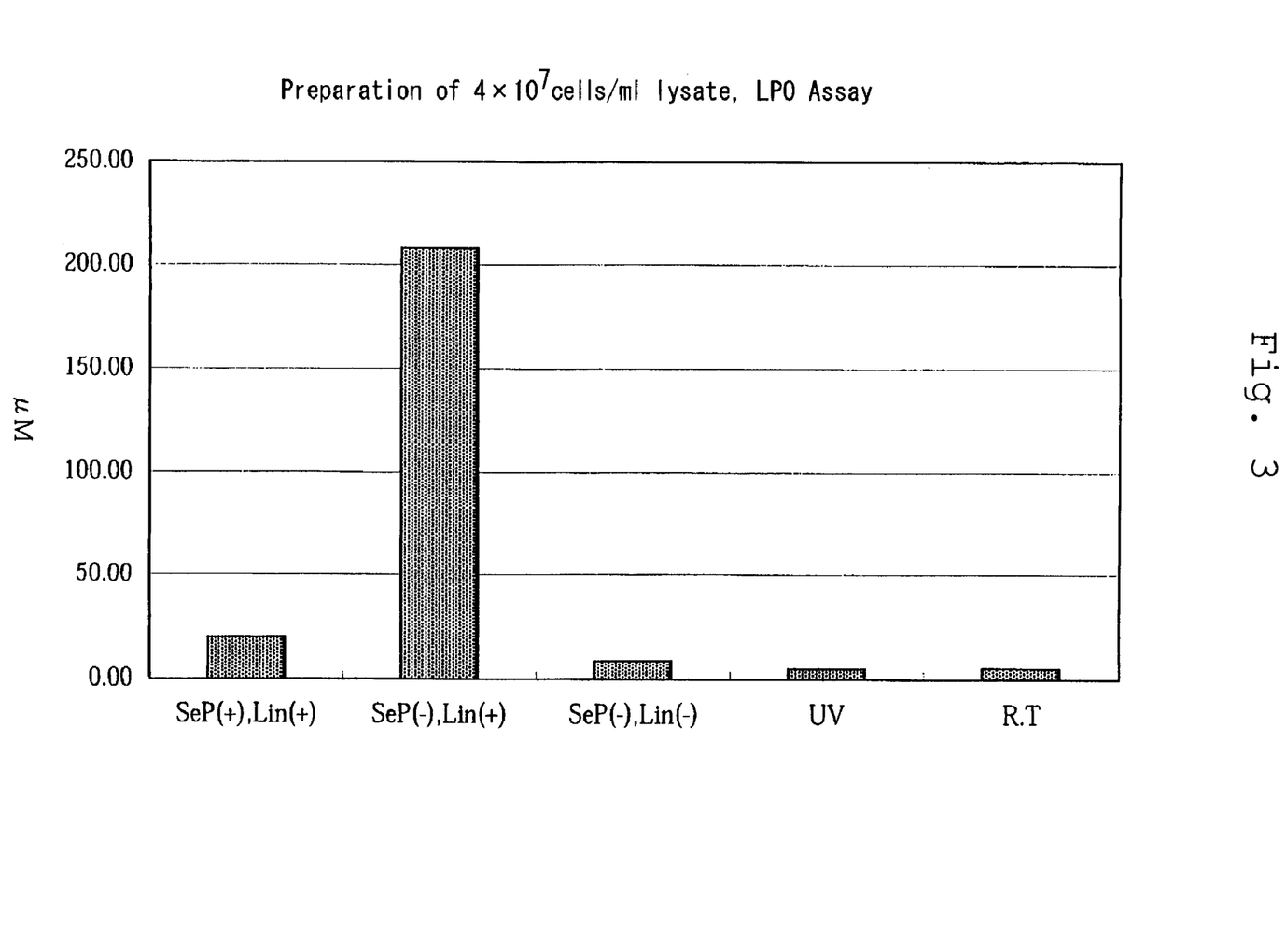
FIG. 3 indicates that inhibition of peroxidized lipid formation can be used as an index of cytotoxicity for assessing the cytotoxicity-inhibitory activity in accordance with the present invention.

As a result, increase in an amount of peroxidized lipids was observed in the system where the selenoprotein P fragment was not added in the presence of linoleic acid whereas increase in an amount of peroxidized lipids was inhibited in the system where the selenoprotein P fragment was added. Also, no increase in an amount of peroxidized lipids was observed in case of cytotoxicity induced by being left to stand at room temperature or by UV radiation. Thus, it was proved that the selenoprotein P fragment inhibited production of peroxidized lipids due to addition of linoleic acid and that an amount of peroxidized lipids could be used as an index of cytotoxicity. See FIG. 3.

EXAMPLE 5

(Increase in Intracellular GPX (Glutathione Peroxidase) Activity)

Dami cells, which can be subcultured in serum free medium SFO3 (manufactured by Sanko Jun-yaku K.K.) containing 0.05 µM 2ME and 0.1% BSA, were cultured in SA/0.01% BSA for more than 96 hours to reduce an intracellular GPX activity. The resulting cells were suspended in SA/0.01% BSA at $5 \times 10^5$ cells/ml. To 1 ml of this cell suspension were added samples at a fixed concentration so as to compare a concentration that was effective for increase in GPX activity in the samples.

Figure 4:
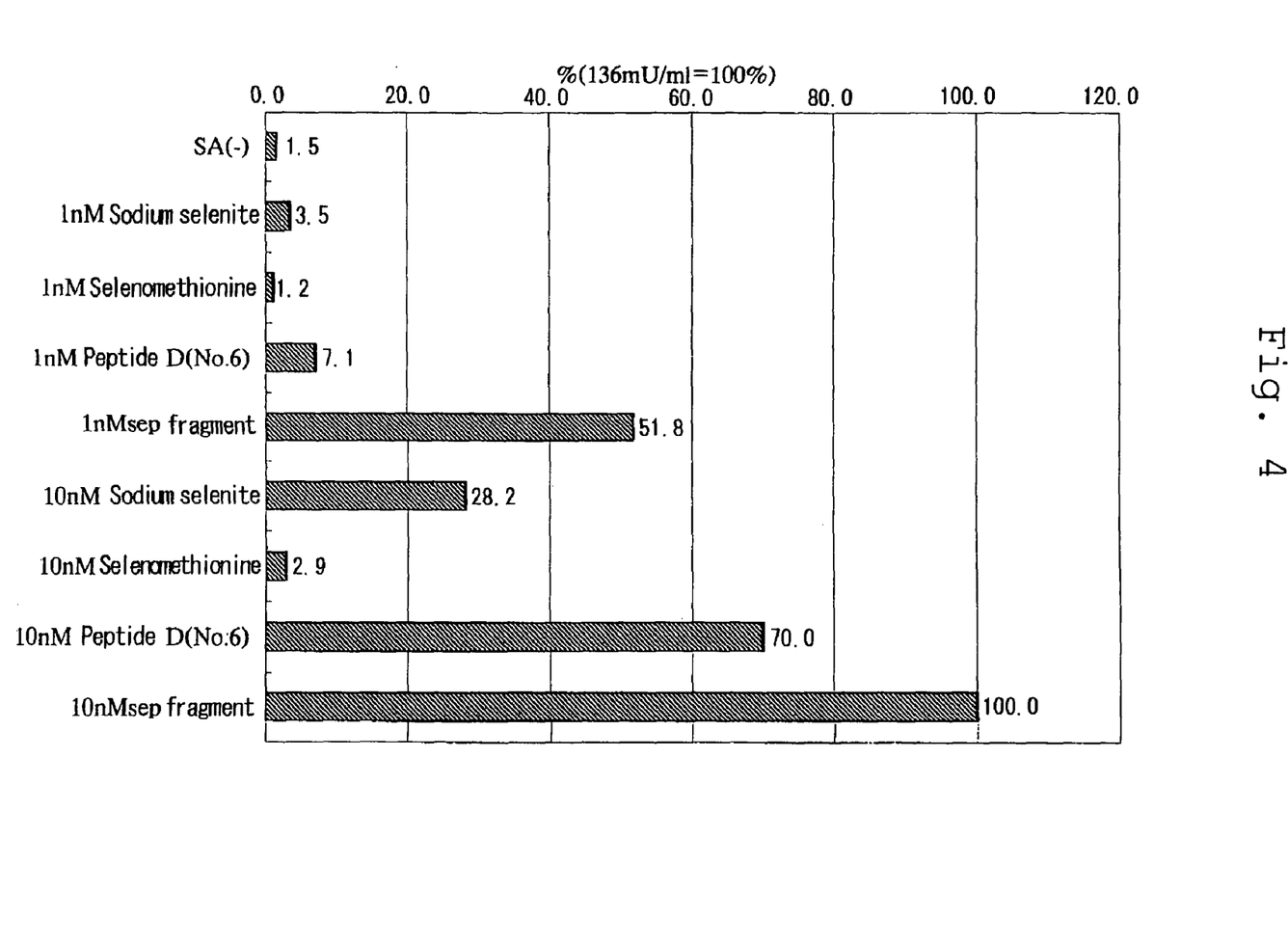
FIG. 4 indicates that increase in a GPX (glutathione peroxidase) activity can be used as an index of cytotoxicity for assessing the cytotoxicity-inhibitory activity in accordance with the present invention.

The samples included a selenoprotein P fragment, a synthetic peptide, selenocystine, selenomethionine, Ebselen and sodium selenite. The effect was compared among these samples. As a result, the selenoprotein P fragment and the synthetic peptide significantly increased the intracellular GPX activity even at 1 nM while selenocystine and sodium selenite exhibited as low as around 50% of increase in the activity. On the contrary, increase in the activity could scarcely be observed in Ebselen and selenomethionine even at 10 nM. See FIG. 4 in which the axis of abscissas indicates a percent GPX activity induced by various samples with the GPX activity induced by addition of 10 nM selenoprotein P fragment being 100% while culture of Dami cells.

As described above, it was proved that selenium compounds that efficaciously functioned to cells could be screened by the method.

The invention claimed is:

1. A method for screening a substance for cytotoxicity-inhibitory activity, which method comprises:
providing a cell culture;
culturing the cells in the cell culture in serum free medium supplemented with albumin or a fatty acid,
inducing cytoxicity in the cells by inducing apoptosis with the albumin or the fatty acid;
contacting a test substance comprising a peptide with the cells in the cell culture;
quantitating glutathione peroxidase (GPX) activity before and after contacting a test substance with the cells; and
assessing an extent of cytotoxicity inhibition after contacting the test substance with the cells,
wherein the GPX activity is inversely correlated with cytotoxicity, and
wherein when the test substance causes an increase in the GPX activity in the cells compared to the GPX activity in the cells before contacting the cells with said test substance, the test substance is thereby identified as a cytotoxicity-inhibitory substance.

2. The method according to claim 1, wherein the cell culture is supplemented with albumin.

3. The method according to claim 1, wherein the cell culture is supplemented with fatty acid.

4. The method according to claim 2, wherein the cell culture comprises 0.01 to 0.5% of albumin.

5. The method according to claim 3, wherein the fatty acid is selected from the group consisting of eicosadienoic acid, dihomo-γ-linolenic acid, docosadienoic acid, docosatrienoic acid, adrenic acid, eicosapentaenoic acid, docosahexaenoic acid, linoleic acid, linolenic acid and arachidonic acid.

6. The method according to claim 1, wherein the cells are from human megakaryoblast cell lines, T cell-derived cell lines, B cell derived cell lines, liver-derived cell lines, nervous system-derived cell lines or kidney-derived cell lines.

7. The method according to claim 1, wherein the cells are from human megakaryoblast cell lines.

8. The method according to claim 1, wherein the cells are from T cell-derived cell lines.

9. The method according to claim 1, wherein the cells are from B cell derived cell lines.

10. The method according to claim 1, wherein the cells are from liver-derived cell lines.

11. The method according to claim 1, wherein the cells are from nervous system-derived cell lines.

12. The method according to claim 1, wherein the cells are from kidney-derived cell lines.

13. The method according to claim 7, where the cells are Dami cells.

14. The method of claim 8, wherein the cells are Molt4, CEM, or Jurkat cells.

15. The method according to claim 9, wherein the cells are P3X63AG8.653 or P3X63AG8.U1 cells.

16. The method according to claim 10, where the cell are HepG2cells.

17. The method according to claim 11, wherein the cells are IMR 32 cells.

18. The method according to claim 12, wherein the cells are CRL 1932 cells.

19. The method according to claim 1, wherein the test substance comprises selenocysteine.

20. The method according to claim 1, wherein an effective concentration of the test substance is about 100 nM and 10 pM.

* * * * *